United States Patent [19]

May

[11] Patent Number: Plant 7,654

[45] Date of Patent: Sep. 17, 1991

[54] CHRYSANTHEMUM PLANT NAMED WHITE SPLENDOR

[75] Inventor: Earl T. May, Los Osos, Calif.

[73] Assignee: May Floral Company, Inc., Los Osos, Calif.

[21] Appl. No.: 556,992

[22] Filed: Jul. 25, 1990

[51] Int. Cl.[5] ..... A01H 5/00

[52] U.S. Cl. ..... Plt./74

[58] Field of Search ..... Plt./74.1, 82.1, 77, Plt./74

[56] References Cited

U.S. PATENT DOCUMENTS

P.P. 7,332 9/1990 Callahan ..... Plt. 74

*Primary Examiner*—Howard J. Locker

*Attorney, Agent, or Firm*—Burns, Doane, Swecker & Mathis

[57] ABSTRACT

A new and distinct cultivar of Chrysanthemum plant named White Splendor is provided. The new cultivar was the result of naturally occurring mutation of unknown causation and is characterized by the formation of attractive pure white ray florets which can be readily distinguished from the light lavender ray florets of the parent Splendor cultivar (U.S. Plant Pat. No. 5,225). The new cultivar is particularly suited for growing as a pot mum.

2 Drawing Sheets

SUMMARY OF THE INVENTION

The present invention comprises a new and distinct cultivar of *Dendranthema morifolium* Ramat., and hereinafter is referred to by the White Splendor cultivar name.

The new cultivar is a mutation of unknown causation which was discovered and carefully preserved during the course of plant selection work which was conducted by me. The new cultivar was discovered among plants of Splendor cultivar (U.S. Plant Pat. No. 5,225) being grown under my direct supervision at Los Osos, Calif., which formed blossoms having the characteristic light lavender ray floret coloration and a flat capitulum form of the daisy type.

More specifically, the selection of the new cultivar was made during the course of a mum production program conducted in greenhouses located at Los Osos, Calif. In such a program, cuttings of the Splendor cultivar were rooted and converted into marketable potted mum plants while using conventional plant growth techniques. On June 22, 1989, it was observed that a portion of one stem on a single plant of the Splendor cultivar having five stems and growing in a 6 inch pot, exhibited one terminal blossom and one blossom below the terminal blossom having distinctive pure white ray florets. All other blossoms exhibited the light lavender ray floret coloration characteristic of the Splendor cultivar. On June 23, 1989, the four stems which exhibited blossoms having exclusively the light lavender coloration were removed, and the observation and study of the stem which exhibited blossoms having a pure white coloration was continued. On July 5, 1989, all blossoms were removed just below the capitulum bases, and the plant was subjected to a long day treatment to encourage the development of new vegetative growth. On Sept. 5, 1989, two vegetative cuttings were removed from the plant and were each rooted in separate four inch pots. On Sept. 21, 1989, these two young plants were subjected to a short day treatment. On Nov. 23, 1989, both of these plants were in flower, and it was observed that one plant exhibited exclusively blossoms having the light lavender ray floret coloration characteristic of the Splendor cultivar and one plant exhibited exclusively blossoms having a pure white ray coloration of the new and distinctive White Splendor cultivar of the present invention. On Dec. 5, 1989, all blossoms on the plant of the White Splendor cultivar were removed below the capitulum bases and the plant was subjected to a long day treatment to encourage the development of new vegetative growth. On Mar. 1, 1990, eleven cuttings were taken from the resulting plant with five cuttings being rooted in six-inch pots and six cuttings being rotted in four-inch pots. On Mar. 19, 1990, all eleven plants were pinched and were subjected to a short day treatment. On May 10, 1990, the blossoms began to open on these plants. In all instances the blossoms exhibited the pure white floral rays characteristic of the White Splendor cultivar of the present invention. Also, all characteristics of the White Splendor other than floral ray coloration are believed to be substantially identical to those of the Splendor cultivar when grown under the same conditions. The new cultivar is particularly well suited for growing as a pot mum.

This asexual reproduction of the new cultivar by cuttings, as performed at Los Osos, Calif., has demonstrated that the characteristics of the new cultivar as herein disclosed are firmly fixed and are retained through successive generations of asexual propagation.

White Splendor has not been observed under all possible environmental conditions to date. Accordingly, it is possible that the phenotype may vary somewhat with variations in the environment, such as temperature, light, day length, contact with pesticides and/or subjection to growth retardant treatments. To date under the controlled conditions described herein, the characteristics of the White Splendor cultivar, other than floral ray coloration, have in all instances been very similar to those of the Splendor cultivar. This combination of characteristics is capable of well distinguishing the new White Splendor cultivar from all other known Chrysanthemum cultivars.

BRIEF DESCRIPTION OF THE PHOTOGRAPHS

The accompanying photographs show as nearly true as it is reasonably possible to make the same in color illustrations of this character, typical specimens of the plant and blossoms of the new cultivar. The plants of the new variety were grown at Los Osos, Calif.

FIG. 1 illustrates a typical specimen of the overall plant of the new cultivar while growing in a 6.5 inch pot wherein the pure white ray florets of the blossoms are apparent, and FIG. 2 illustrates for comparative purposes the pure white ray florets of the blossoms of the White Splendor cultivar at the top and the light lavender ray florets of the parent Splendor cultivar (U.S. Plant Pat. No. 5,225) at the bottom while growing in 6.5 inch pots. In each instance the blossoms have a flat capitulum form and are of the daisy capitulum type.

DETAILED DESCRIPTION

Figure 1:
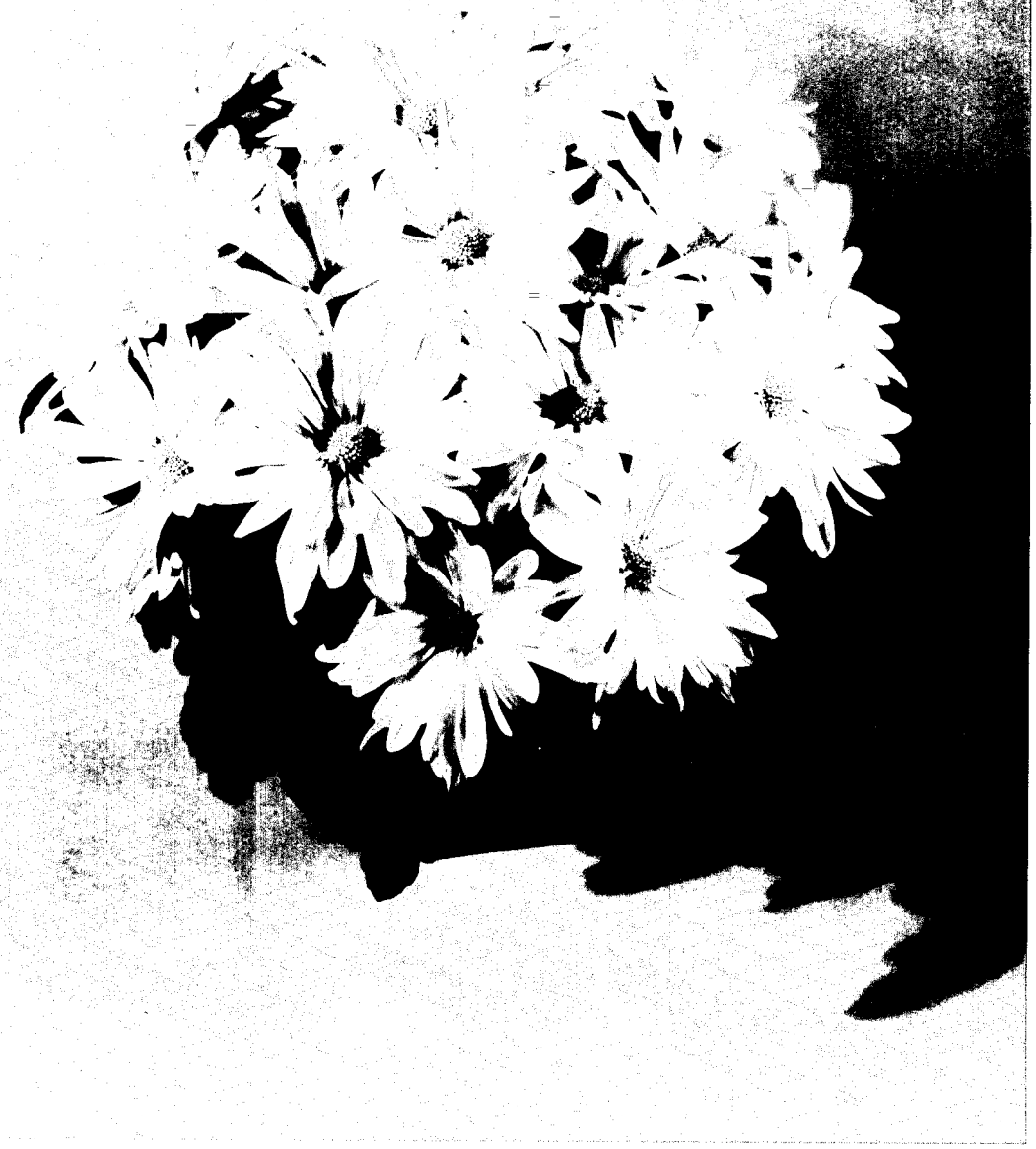
Figure 2:
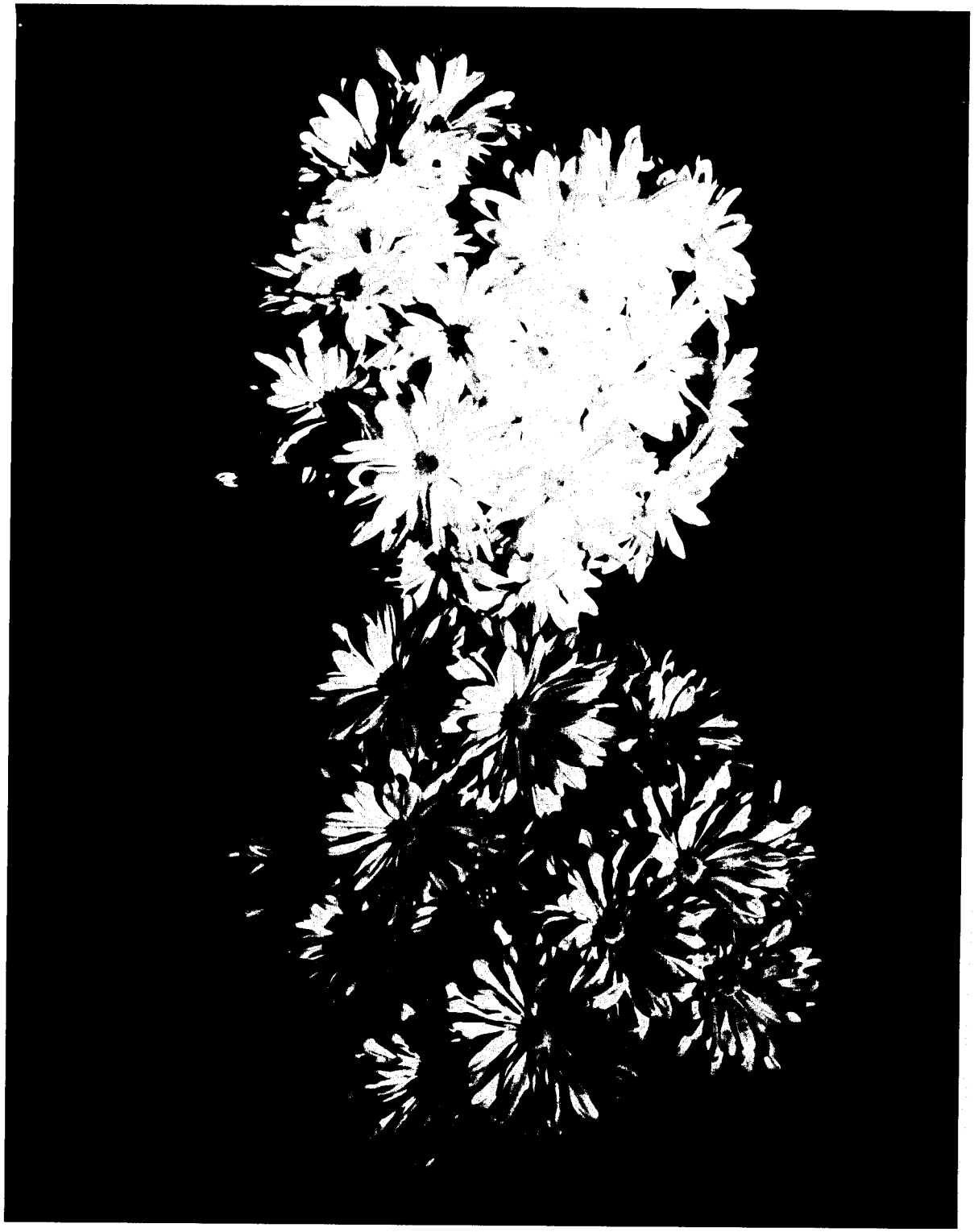

The charts used in the identification of colors described hereafter are The R.H.S. Colour Chart and the Panatone Color Chart. The color values were determined at 11:00 a.m. and at 12 noon under indirect light conditions on June 6, 1990 at Lompoc, Calif.

Classification:

*Botanical.*—*Dendranthema morifolium* Ramat., cv. White Splendor.

*Commercial.*—Pot mum.

Inflorescence:

A. Capitulum:

*Form.*—Flat.

*Type.*—Daisy or single.

*Diameter across face.*—Approximately 12 to 13 cm. on average.

B. Corolla of ray florets:

*Color (generally tonality from a distance of one meter).*—Pure white.

*Color (front).*—Pure white, whiter than White Group 155D of The R.H.S. Colour Chart.

*Color (back).*—Pure white, whiter the White Group 155D of The R.H.S. Colour Chart.

C. Corolla of disc florets

*Color (immature).*—Greenish-yellow.

*Color (mature).*—Yellow, 396C of the Panatone Color Chart.

D. Reproductive organs

*Androecium.*—Stamens are included only in the corolla of the disc florets; pollen production is insignificant.

*Gynoecium.*—Superior, one-celled and basal.

Plant

A. General appearance:

*Height.*—Commonly varies between 7 to 30 cm. above the edge of the pot depending on the size of the pot and the growing conditions. The smaller heights commonly are associated with the use of smaller pot sizes. Typical growing conditions when using four-inch pots are two long-day weeks before pinch and ligths out, and 1 to 3 applications of 2500 B-9 growth regulator after lights out. Typical growing conditions when using six-inch pots are two long-day weeks before pinch, one long-day week following pinch and lights out, and 1 to 3 applications of 2500 B-9 growth regulator after lights out.

B. Foliage:

*Color (front).*—Yellor-Green Group 147A of The R.H.S. Colour Chart, and 553C of the Panatone Color Chart.

*Color (back).*—Green Group 137B of The R.H.S. Colour Chart, and 575U of the Panatone Color Chart.

*Shape.*—Simple, ovate with cuneate base.

*Margin.*—Moderately lobed and pinnately parted and crenate with an obtuse tip.

CHART A

COMPARISON OF TYPICAL CHARACTERISTICS OF FINISHED PLANT

| | Splendor | White Splendor |
|---|---|---|
| Diameter of Capitulum: | 12 to 13.5 cm. | 12 to 13 cm. |
| Diameter of Disc. | 1.8 cm. | 1.5 cm. |
| Thickness of Disc. | 1.2 cm. | 1.2 cm. |
| Average Number of Ray Florets | 37 | 37 |
| Length of Ray Corolla | 5.6 cm. | 5.5 cm. |
| Width of Ray Corolla | 1.4 cm. | 1.2 cm. |
| Color of Ray Corolla (front and back) | Light Lavender | Whiter than White Group 155D of R.H.S. Colour Chart |
| Length of Disc Corolla | 0.7 cm. | 0.7 cm. |
| Color Disc Corolla (immature) | Green-Yellow | Green-Yellow |
| Color Disc Corolla (mature) | Yellow | Yellow |
| Number of Flowers Per Stem. | 4.5 | 4.5 |
| Color of Foliage (front) | Yellow-Green Group 147A of R.H.S. Colour Chart | Yellow-Green Group 147A of R.H.S. Colour Chart |
| Color of Foliage (back) | Green Group 137B of R.H.S. Colour Chart | Green Group 137B of R.H.S. Colour Chart |
| Length of Largest Leaf | 13.5 cm. | 11.5 cm. |
| Width of Largest Leaf | 8.5 cm. | 7.0 cm. |
| Flowering Respose Period | 9 weeks | 9 weeks |
| Treatment Required | Medium | Medium |

I claim:

1. A new and distinct cultivar of Chrysanthemum plant named White Splendor, substantially as herein shown and described, which exhibits pure white ray florets in combination with other characteristics which are substantially identical to those of the Splendor cultivar (U.S. Plant Pat. No. 5,225).

* * * * *